United States Patent [19]
Muller et al.

[11] Patent Number: 6,011,040
[45] Date of Patent: Jan. 4, 2000

[54] USE OF TETRAHYDROFOLATES IN NATURAL STEREOISOMERIC FORM FOR THE PRODUCTION OF A PHARMACEUTICAL PREPARATION SUITABLE FOR INFLUENCING THE HOMOCYSTEINE LEVEL, PARTICULARLY FOR ASSISTING THE REMETHYLATION OF HOMOCYSTEINE

[75] Inventors: Hans Rudolf Muller, Schaffhausen; Martin Ulmann, Dachsen; Rudolf Moser, Schaffhausen, all of Switzerland

[73] Assignee: Eprova AG, Schaffhausen, Switzerland

[21] Appl. No.: 09/095,572

[22] Filed: Jun. 11, 1998

[30] Foreign Application Priority Data

Jun. 13, 1997 [CH] Switzerland .............................. 1456/97

[51] Int. Cl.[7] .................................................. A61K 31/505

[52] U.S. Cl. ............................................................ 514/258

[58] Field of Search ............................................. 514/258

[56] References Cited

U.S. PATENT DOCUMENTS 5,334,535   8/1994   Schlingmann et al. .................. 435/280

FOREIGN PATENT DOCUMENTS 595005   9/1993   European Pat. Off. .
97/27764   1/1996   WIPO .

OTHER PUBLICATIONS

Resch (ed.), Risikofaktor Homocystein Daten–Fakten–Strateien [Homocystein Risk Factor—Data–Facts–Strategies], Gesellschaft für Medizinische Information ISBN 3–980 45 36–0–C. (1996).

Fortin et al., Clinical Biochemistry, 28(2):155–162, 1995.

Mills et al., Supplement Publication to the Ceres Form on Jun. 14, 1995, 1996, pp. 756S–760S.

Loehrer, F.M., Abstract from Arterioscler Thromb Vasc Bio., "Low whole–blood S–adenosylmethionine and correlation between 5–methyltetrahydrofolate and homocysteine in coronary artery disease", 16:6, Jun. 1996, pp. 727–733.

Primary Examiner—Raymond Henley, III
Attorney, Agent, or Firm—Millen, White, Zelano, & Branigan, P.C.

[57] ABSTRACT

This invention relates to the use of tetrahydrofolates in natural stereoisomeric form for the production of a pharmaceutical preparation suitable for influencing the homocysteine level, particularly for assisting the remethylation of homocysteine. Clinical areas of application include all anomalies of the homocysteine level, particularly the prevention and treatment of cardiovascular diseases and the prevention of neural tube deficiencies. The present invention also relates to pharmaceutical preparations comprising at least one compound selected from the group consisting of 5-formyl-(6S)-tetrahydrofolic acid, 5-methyl-(6S)-tetrahydrofolic acid, 5,10-methylene-(6R)-tetrahydrofolic acid, 5,10-methenyl-(6R)-tetrahydrofolic acid, 10-formyl-(6R)-tetrahydrofolic acid, 5-formimino-(6S)-tetrahydrofolic acid or (6S)-tetrahydrofolic acid or pharmaceutically compatible salts thereof, together with pharmaceutically compatible active and adjuvant substances, for influencing the homocysteine level, particularly when a methylene tetrahydrofolate reductase deficiency exists, such as when thermolabile methylene tetrahydrofolate reductase exists for example.

22 Claims, No Drawings

USE OF TETRAHYDROFOLATES IN NATURAL STEREOISOMERIC FORM FOR THE PRODUCTION OF A PHARMACEUTICAL PREPARATION SUITABLE FOR INFLUENCING THE HOMOCYSTEINE LEVEL, PARTICULARLY FOR ASSISTING THE REMETHYLATION OF HOMOCYSTEINE

This invention relates to the use of tetrahydrofolates in natural stereoisomeric form for the production of a pharmaceutical preparation suitable for influencing the homocysteine level, particularly for assisting the remethylation of homocysteine. Clinical areas of application include all anomalies of the homocysteine level, particularly the prevention and treatment of cardiovascular diseases and the prevention of neural tube deficiencies.

In the present text, the expression "tetrahydrofolates in natural stereoisomeric form" refers to 5-formyl-(6S)-tetrahydrofolic acid, 5-methyl-(6S)-tetrahydrofolic acid, 5,10-methylene-(6R)-tetrahydrofolic acid or (6S)-tetrahydrofolic acid or pharmaceutically compatible salts thereof.

As drugs, tetrahydrofolates have predominantly been used hitherto as the calcium salt of 5-formyl-5,6,7,8-tetrahydrofolic acid (leucovorin) or of 5-methyl-5,6,7,8-tetrahydrofolic acid for the treatment of megaloblastic folic acid deficiency anemia, as an antidote for increasing the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatoid arthritis, for increasing the compatibility of certain antiparasitic agents, for instance trimethoprim-sulfamethoxazole, and for decreasing the toxicity of dideaza-tetrahydrofolates in chemotherapy.

Homocysteine is a thiol-containing amino acid which is formed on the demethylation of methionine. In body fluids, homocysteine exists in oxidised form as a disulphide (homocystine), as mixed disulphides and as a cyclised oxidation product (homocysteine thiolactone).

Hyperhomocysteineniia is a clinical disorder which may have various congenital or acquired causes. These disorders result in an increased concentration of homocysteine in the blood and in the urine.

The commonest form of hyperhomocysteinemia results from a deficiency of cystathione β-synthase, an enzyme involved in the $B_6$-dependent transulphuration pathway, in which homocysteine is converted into cysteine via cystathionine. Another form is due to a deficiency of 5,10-methylene tetrahydrofolate reductase, which provides the substrate, 5-methyl-(6S)-tetrahydrofolic acid, for the $B_{12}$-dependent conversion of homocysteine to methionine. Hyperhomocysteinemia can also occur as a consequence of functional disorders of the kidneys. In all these cases, the term "hyperhomocysteinemia" refers to a temporary or permanent increase in the homocysteine level in the blood, which is sometimes accompanied by an increased urinary secretion of homocysteine.

Hyperhomocysteinemia results in a series of diseases, which are manifested in severe vascular, ocular, neurological and skeletal disorders.

Various clinical studies have shown a clear connection between an increased homocysteine level in the serum and the development of cardiovascular diseases. Homocysteinemia is considered to be an independent risk factor in cardiovascular diseases. General information can be found in K. L. Resch (ed.), Risikofaktor Homocystein Daten-Fakten-Strategien [*Homocysteine Risk Factor—Data-Facts-Strategies*], Gesellschaft für Medizinische Information ISBN 3-980 45 36-0-X. Reference is made to L. J. Fortin et al, Clinical Biochemistry, Vol. 28(2), 1995, pages 155–162 as regards the relationship between hyperhomocysteinemia and arteriosclerosis. Maternal hyperhomocysteinemia and prenatal neural tube deficiency have been described by J. L. Mills et al., Supplement Publication to the Ceres Forum on Jun. 14, 1995, 1996, pages 756S–760S.

The use of tetrahydrofolates in natural stereoisomeric form for the production of a pharmaceutical preparation suitable for influencing the homocysteine level has neither been proposed nor described hitherto.

It has been found that the use of pharmaceutical preparations containing the natural stereoisomeric form of tetrahydrofolates influences the homocysteine level, and in particular assists the remethylation of homocysteine.

The natural stereoisomeric form of tetrahydrofolates refers to 5-formyl-(6S)-tetrahydrofolic acid, 5-methyl-(6S)-tetrahydrofolic acid, 5,10-methylene-(6R)-tetra-hydrofolic acid, 5,10-methenyl-(6R)-tetrahydrofolic acid, 10-formyl-(6R)-tetrahydrofolic acid, 5-formimino-(6S)-tetrahydrofolic acid or (6S)-tetrahydrofolic acid or pharmaceutically compatible salts thereof. Reduced folates are used, which as a rule can generally be mutually transformed into one another in the folate metabolism. 5-methyl-(6S)-tetrahydrofolic acid and the pharmaceutically compatible salts thereof are preferably used, however, since 5-methyl-(6S)-tetrahydrofolic acid is directly involved, as a methyl donor, in the transfer of the methyl group of homocysteine to methionine. This applies in particular when there is an existing methylene tetrahydrofolate reductase deficiency, wherein this deficiency implies disorders such as restricted functionality or lack of activity, for example. The existence of thermolabile methylene tetrahydrofolate reductase should be mentioned here as the most frequent example of a methylene tetrahydrofolate reductase deficiency. Under these circumstances, tetrahydrofolates can only be converted to a limited extent and can thus only be used in conjunction in the methylation reaction to a limited extent.

Pharmaceutically compatible salts should be both pharmacologically and pharmaceutically compatible. Pharmacologically and pharmaceutically compatible salts such as these may be alkali or alkaline earth metal salts, preferably sodium, potassium, magnesium or calcium salts.

The expression "pharmaceutical preparations" refers to enteral (e.g. oral, sublingual or rectal), parenteral or topical (e.g. transdermal) forms. Organic or inorganic substances which do not react with the active ingredient can be used as supports, e.g. water, oil, benzyl alcohol, polyethylene glycol, glycerol triacetate or other fatty acid glycerides, gelatine, lecithin, cyclodextrin, carbohydrates such as lactobiose or starch, magnesium stearate, talc or cellulose. Tablets, dragees, capsules powders, syrup concentrates or drops are preferred for oral application, suppositories are preferred for rectal application, and water- or oil-based solutions or lyophilisates are preferably used for parenteral application. Suspensions, emulsions or implants can also be used, and patches or creams can be used for topical application.

Pharmaceutical preparations for parenteral application comprise sterile aqueous and non-aqueous injection solutions of the pharmaceutically-active compounds, which are preferably isotonic with the blood of the recipient.

These preparations may comprise stabilisers, additives for the controlled release of the pharmaceutically-active compounds, antioxidants, buffers, bacteriostatic agents and adjuvant substances for obtaining an isotonic solution. Aqueous and non-aqueous sterile suspensions may contain suspension additives and thickeners. The pharmaceutical preparation may exist as a single dose- or as a multiple-dose container, as sealed ampoules for example, and may be stored as a freeze-dried (lyophilised) product and prepared for use if need be with a sterile liquid, for example water or salt solution. Sterile powders, granules or tablets can be used in the same manner. All the pharmaceutical preparations may additionally contain active compounds which act separately or synergistically. Vitamins should be mentioned here, especially those from the vitamin B group, such as $B_6$ and/or $B_{12}$, which have a synergistic effect in this application. In this respect, vitamin $B_6$ can be used in a dose between 1 mg and 20 mg, preferably between 1 mg and 6 mg per day, for a normal dosage application, and can be used in a dose between 6 mg and 20 mg per day for a high dosage application. Vitamin $B_{12}$ can be used in a dose between 0.001 mg and 0.5 mg, preferably between 0.001 mg and 0.15 mg per day, for a normal dosage application, and can be used in a dose between 0.15 and 0.5 mg per day for a high dosage application.

The pharmaceutical preparation contains between 0.001 mg and 1000 mg of the active ingredient per dose. In prophylaxis, preparations are used which preferably contain between 5 µg and 1000 µg of the active ingredient per dose. In therapy, preparations are used which preferably contain between 0.1 mg and 200 mg of the active ingredient per dose.

The dosage depends on the form of therapy, on the form of application of the pharmaceutical preparation, and on the age, weight, nutrition and condition of the patient. Treatment may be commenced with a low dosage below the optimum amount and this may be increased until the optimum effect is achieved. The dosages used in prophylaxis may preferably vary between 5 µg and 1000 µg per day, particularly between 50 µg and 500 µg per day. Optimum dosages in therapy vary between 0.1 mg and 100 mg per day, particularly between 0.5 mg and 5 mg per day. Application may be effected as a single administration or as a repeated dosage.

EXAMPLES TO ILLUSTRATE THE INVENTION

Example 1

A tablet containing 1 mg 5-formyl-(6S)-tetrahydrofolic acid

A mixture of 13.3 g of the pentahydrate of the calcium salt of 5-formyl-(6S)-tetrahydrofolic acid (corresponding to 10 g 5-formyl-(6S)-tetrahydrofolic acid), 4 kg lactose, 1.2 kg starch, 0.2 kg talc and 0.1 kg magnesium stearate is pressed to form tablets, so that each tablet contains I mg 5-formyl-(6S)-tetrahydrofolic acid.

The tablet can be coated as a film tablet or can be ground and used in capsule form.

Example 2

A suppository containing 60 mg 5-methyl-(6S)-tetrahydrofolic acid

A mixture of 632 g of the pentahydrate of the calcium salt of 5-methyl-(6S)-tetrahydrofolic acid (corresponding to 500 g 5-methyl-(6S)-tetrahydrofolic acid), 50 g hydroxypropylcellulose and 2 kg of semisynthetic glycerides is melted to form suppositories, so that each suppository contains 500 mg 5-methyl-(6S)-tetrahydrofolic acid.

Example 3

An injection solution containing 0.5 mg 5-methyl-(6S)-tetrahydrofolic acid 0.5 g 5-methyl-(6S)tetrahydrofolic acid, 10 g glutathione, 30 g citric acid, 160 g mannitol, 1 g methyl-p-hydroxybenzoic acid, 17.7 g sodium hydroxide (or the requisite amount in order to obtain a pH of the solution of 7.3 to 7.8) is dissolved in 3 liters of water for injection and introduced into ampoules, so that each ampoule contains 0.5 mg 5-methyl-(6S)-tetrahydrofolic acid.

Example 4

An injectable lyophilisate containing 1 mg (6S)-tetrahydrofolic acid

A solution of 1 g of the sodium salt of (6S)-tetrahydrofolic acid in 1000 ml double-distilled water is introduced via sterile filtration into ampoules and lyophilised, so that each ampoule contains 1 mg (6S)-tetrahydrofolic acid.

Tetrahydrofolic acid is very sensitive to oxygen, and stringently oxygen-free conditions therefore have to be employed. The use of an antioxidant such as ascorbic acid may be necessary.

Example 5

An injectable lyophilisate containing 20 mg 5,10-methylene-(6R)-tetrahydrofolic acid A solution of 10 g of the β-hydroxypropyl-cyclodextrin inclusion compound of the sodium salt of 5,10-methylene-(6R)-tetrahydrofolic acid in 2000 ml of double-distilled water is introduced via sterile filtration into ampoules, so that each ampoule contains 20 mg 5,10-methylene-(6R)-tetrahydrofolic acid.

The same precautionary measures apply to 5,10-methylene-tetrahydrofolic acid as for tetrahydrofolic acid (Example 4).

Example 6

A tablet containing 0.4 mg 5-formyl-(6S)-tetrahydrofolic acid

A mixture of 5.32 g of the pentahydrate of the calcium salt of 5-formyl-(6S)-tetrahydrofolic acid (corresponding to 4 g 5-formyl-(6S)-tetrahydrofolic acid), 4 kg lactose, 1.2 kg starch, 0.2 kg talc and 0.1 kg magnesium stearate is pressed to form tablets, so that each table contains 4 mg 5-formyl-(6S)-tetrahydrofolic acid.

The tablet can be coated as a film tablet or can be ground and used in capsule form.

Example 7

An injectable lyophilisate containing 10 µg 6-methyl-(6S)-tetrahydrofolic acid

A solution of 10 mg of the sodium salt of 5-methyl-(6S)-tetrahydrofolic acid in 1000 ml of double-distilled water is introduced, via sterile filtration under an inert gas, into ampoules and lyophilised, so that each ampoule contains 10 µg 5-methyl-(6S)-tetrahydrofolic acid.

Tetrahydrofolic acid is very sensitive to oxygen, and stringently oxygen-free conditions therefore have to be employed. The use of an antioxidant such as ascorbic acid may be necessary.

Example 8

A tablet containing 15 mg 5-methyl-(6S)-tetrahydrofolic acid

A mixture of 19.18 g of the pentahydrate of the calcium salt of 5-methyl-(6S)-tetrahydrofolic acid (corresponding to 15 g 5-methyl-(6S)-tetrahydrofolic acid), 120 g lactose, 21.5 g maize starch, 7.08 g acetylcellulose, 2.28 g diethyl phthalate, 0.64 g silicone HK-15 and 2 g magnesium stearate is pressed to form tablets, so that each tablet contains 15 mg 5-methyl-(6S)-tetrahydrofolic acid.

The tablet can be coated as a film tablet or can be ground and used in capsule form.

Example 9
Tablets containing 15 mg 5-methyl-(6S)-tetrahydrofolic acid

In an analogous manner to that described in Example 8, tablets containing 15 mg 5-methyl-(6S)-tetrahydrofolic acid are produced using maize starch, lactose, magnesium stearate, polyethylene glycol 6000, polymethacrylate, polysorbitol 80, dimethylpolysiloxane, sodium hydroxide and talc.

Example 10
A combination preparation comprising 5-methyl-(6S)-tetrahydrofolic acid, vitamin $B_6$ and vitamin $B_{12}$ A film tablet which contains the following constituents is formulated for preparations for oral application:

| | |
|---|---|
| 0.4 mg | 5-methyl-(6S)-tetrahydrofolic acid |
| 3 mg | vitamin $B_6$ |
| 0.002 mg | vitamin $B_{12}$ |
| | pharmaceutically compatible adjuvant substances |

This combination preparation may also be formulated as a solution, e.g. for parenteral application.

What is claimed is:

1. A method of decreasing homocysteine levels in the human body comprising administering at least one tetrahydrofolate in natural stereoisomeric form to a human subject.

2. A method of preventing or treating disease associated with increased levels of homocyteine levels in the human body comprising administering at least one tetrahydrofolate in natural stereoisomeric form to a human subject.

3. A method according to claim 2, wherein the disease is cardiovascular disease.

4. A method of preventing prenatal neural tube deficiencies associated with increased maternal homocysteine levels comprising administering at least one tetrahydrofolate in natural stereoisomeric form to a female human subject.

5. A method according to claim 2, wherein the tetrahydrofolate is 5-formyl-(6S)-tetrahydrofolic acid, 5-methyl-(6S)-tetrahydrofolic acid, 5,10-methylene-(6R)-tetrahydrofolic acid, 5,10-methenyl-(6R)-tetrahydrofolic acid, 10-formyl-(6R)-tetrahydrofolic acid, 5-formimino-(6S)-tetrahydrofolic acid or (6S)-tetrahydrofolic acid, or salts thereof.

6. A method according to claim 3, wherein the tetrahydrofolate is 5-formyl-(6S)- tetrahydrofolic acid, 5-methyl-(6S)-tetrahydrofolic acid, 5,10-methylene-(6R)-tetrahydrofolic acid, 5,10-methenyl-(6R)-tetrahydrofolic acid, 10-formyl-(6R)-tetrahydrofolic acid, 5-formimino-(6S)-tetrahydrofolic acid or (6S)-tetrahydrofolic acid, or salts thereof.

7. A method according to claim 4, wherein the tetrahydrofolate is 5-formyl-(6S)-tetrahydrofolic acid, 5-methyl-(6S)-tetrahydrofolic acid, 5,10-methylene-(6R)-tetrahydrofolic acid, 5,10-methenyl-(6R)-tetrahydrofolic acid, 10-formyl-(6R)-tetrahydrofolic acid, 5-formimino-(6S)-tetrahydrofolic acid or (6S)-tetrahydrofolic acid, or salts thereof.

8. A method according to claim 2, wherein the tetrahydrofolate is 5-methyl-(6S)-tetrahydrofolic acid, or a salt thereof.

9. A method according to claim 3, wherein the tetrahydrofolate is 5-methyl-(6S)-tetrahydrofolic acid, or a salt thereof.

10. A method according to claim 4, wherein the tetrahydrofolate is 5-methyl-(6S)-tetrahydrofolic acid, or a salt thereof.

11. A method according to claim 2, wherein increased levels of homocysteine in the human body are associated with methylene tetrahydrofolate reductase deficiency and wherein the tetrahydrofolate is 5-methyl-(6S)-tetrahydrofolic acid, or a salt thereof.

12. A method according to claim 3, wherein increased levels of homocysteine in the human body are associated with methylene tetrahydrofolate reductase deficiency and wherein the tetrahydrofolate is 5-methyl-(6S)-tetrahydrofolic acid, or a salt thereof.

13. A method according to claim 4, wherein increased levels of homocysteine in the human body are associated with methylene tetrahydrofolate reductase deficiency and wherein the tetrahydrofolate is 5-methyl-(6S)-tetrahydrofolic acid, or a salt thereof.

14. A method according to claim 2, wherein increased levels of homocysteine in the human body are associated with thermolabile methylene tetrahydrofolate reductase deficiency and wherein the tetrahydrofolate is 5-methyl-(6S)-tetrahydrofolic acid, or a salt thereof.

15. A method according to claim 3, wherein increased levels of homocysteine in the human body are associated with thermolabile methylene tetrahydrofolate reductase deficiency and wherein the tetrahydrofolate is 5-methyl-(6S)-tetrahydrofolic acid, or a salt thereof.

16. A method according to claim 4, wherein increased levels of homocysteine in the human body are associated with thermolabile methylene tetrahydrofolate reductase deficiency and wherein the tetrahydrofolate is 5-methyl-(6S)-tetrahydrofolic acid, or a salt thereof.

17. A method according to claim 4, wherein the tetrahydrofolate is administered prior to conception.

18. A method according to claim 4, wherein the tetrahydrofolate is administered after conception.

19. A method according to claim 5, wherein the tetrahydrofolate is administered in combination with at least one pharmaceutically compatible active substance or at least one pharmaceutically compatible adjuvant substance.

20. A method according to claim 19, wherein the pharmaceutically compatible active substance comprises at least one B-vitamin.

21. A method according to claim 11, wherein the tetrahydrofolate is administered in combination with at least one pharmaceutically compatible active substance or at least one pharmaceutically compatible adjuvant substance.

22. A method according to claim 21, wherein the pharmaceutically compatible active substance comprises at least one B-vitamin.

* * * * *